(12) United States Patent
Sheth et al.

(10) Patent No.: US 8,865,213 B2
(45) Date of Patent: Oct. 21, 2014

(54) MODIFIED RELEASE PHARMACEUTICAL COMPOSITIONS

(75) Inventors: Nitin Vadilal Sheth, Raleigh, NC (US); Sunil Suresh Jog, Maharashtra (IN); Santosh Sadashiv Chothe, Maharashtra (IN); Sampada Hemant Tupe, Maharashtra (IN)

(73) Assignees: USV Limited (IN); Indicus Pharma LLC, Raleigh, NC (US)

( * ) Notice: Subject to any disclaimer, the term of this patent is extended or adjusted under 35 U.S.C. 154(b) by 435 days.

(21) Appl. No.: 12/981,077

(22) Filed: Dec. 29, 2010

(65) Prior Publication Data

US 2011/0159093 A1    Jun. 30, 2011

(30) Foreign Application Priority Data

Dec. 30, 2009  (IN) .......................... 3018/MUM/2009

(51) Int. Cl.
| | |
|---|---|
| *A61K 9/26* | (2006.01) |
| *A61K 9/14* | (2006.01) |
| *A61K 9/50* | (2006.01) |
| *A61K 31/4422* | (2006.01) |
| *A61K 9/20* | (2006.01) |

(52) U.S. Cl.
CPC ............ *A61K 31/4422* (2013.01); *A61K 9/5078* (2013.01); *A61K 9/5042* (2013.01); *A61K 9/5084* (2013.01); *A61K 9/5026* (2013.01); *A61K 9/2081* (2013.01)
USPC .......................... 424/469; 424/489; 514/264.1

(58) Field of Classification Search
USPC ................................ 424/489, 469; 514/264.1
See application file for complete search history.

(56) References Cited

U.S. PATENT DOCUMENTS

| | | | | |
|---|---|---|---|---|
| 4,892,741 | A * | 1/1990 | Ohm et al. .................... | 424/479 |
| 6,897,205 | B2 * | 5/2005 | Beckert et al. ................ | 514/159 |
| 2004/0126358 | A1 * | 7/2004 | Warne et al. .................. | 424/85.2 |
| 2005/0020613 | A1 * | 1/2005 | Boehm et al. ................. | 514/282 |

* cited by examiner

*Primary Examiner* — Ali Soroush

(74) *Attorney, Agent, or Firm* — Schwegman Lundberg & Woessner , P.A.

(57) ABSTRACT

Disclosed herein are multiparticulate modified release pharmaceutical compositions comprising: (a) a first portion comprising an active ingredient, at least one surfactant and at least one release modifying agent and (b) a second portion comprising an active ingredient and optionally a release modifying agent. Particularly, the active ingredient in the first portion is a calcium channel blocker and the modified release composition is in the form of a multiparticulate tablet.

25 Claims, 2 Drawing Sheets

MODIFIED RELEASE PHARMACEUTICAL COMPOSITIONS

RELATED APPLICATION

This application claims the benefit of Indian Provisional Application No. 3018/MUM/2009, filed on Dec. 30, 2009, Entitled: MODIFIED RELEASE PHARMACEUTICAL COMPOSITIONS, which application is incorporated in its entirety.

TECHNICAL FIELD OF THE INVENTION

The present invention relates to multiparticulate modified release compositions. More particularly, the invention relates to solid oral dosage forms comprising multiparticulate modified release compositions.

BACKGROUND OF THE INVENTION

Multiparticulate drug delivery systems are dosage form, which consists of multiple small discrete units, where each unit exhibits some intended characteristics. Multiparticulates are well-known dosage forms that comprise a plurality of particles for different therapeutic use of the drug.

Modified release formulation aims at minimizing the peak-to-trough variation in drug plasma levels that are associated with conventional frequent dosage regimes.

Several attempts have been made to develop formulations that provide a zero-order release of the drug compound. Most of the modified release formulations today offer the release profile as a zero order, first order or have a delayed release profile. Combination of different types of release i.e. either extended-release or delayed-release and combinations thereof can be achieved by multiparticulates in the dosage form. However these also offer difficulty in achieving the right combination of pellets/particles or where a very high dose needs to be given.

U.S. Pat. No. 4,892,741 discloses solid medicament preparation having a long-lasting action in the form of a press coated tablet which containing dihydropyridine. The press coated tablet comprises (a) a core which contains a dihydropyridine in rapid-release form, and (b) a coat around the core, the coat containing a dihydropyridine in slow-release form.

US2006210631 discloses a multi-particulate, modified-release pharmaceutical composition for the oral administration of an active ingredient to the colon, said particles comprising a core comprising an active ingredient or a pharmaceutically acceptable salt or ester thereof, and optionally one or more excipients; a first coating applied to the surface of the core, wherein said first coating is insoluble in gastric juice and in intestinal juice below pH 7, but soluble in colonic intestinal juice; and a second coating applied to the surface of the first coating.

Studies have shown that there are adverse effects with the coat-core systems compared to other drug delivery systems. Further, the core-coat technology requires the use of specialized equipment thereby rendering an expensive process of manufacture.

Therefore, there still exists a need to formulate modified release formulations containing two different portions of active ingredient which will provide for modified release of the active ingredient and which will have reduced or no adverse effects compared to prior art compositions. There also exists a need to develop process which could be simple and cost effective and would not involve any tedious techniques.

There exists a need for an improved multiparticulate formulation that would improve the bioavailability and release rate and would ameliorate the drawbacks of prior art compositions.

OBJECT OF INVENTION

One object of the invention is to provide a multiparticulate modified release pharmaceutical composition comprising: (a) a first portion and (b) a second portion, wherein the active ingredient in the first and second portion is same or belong to a different therapeutic class.

Another object of the invention is to provide multiparticulate modified release compositions in which a first portion of the active ingredient is released in a delayed manner upon administration and a second portion of the active ingredient is released in an extended manner.

Another object of the invention is to provide multiparticulate modified release composition comprising: (a) a first portion providing the release of the active ingredient in a delayed manner and (b) a second portion providing the release of the active ingredient in an extended manner; wherein the active ingredient present in the first portion and that of the second portion is a Dihydropyridine calcium channel blocker, such as Nisoldipine.

Yet another object of the invention is to provide multiparticulate modified release compositions in which the active ingredient in the first portion is a calcium channel blocker and the active ingredient present in the second portion is selected from the group comprising angiotensin-converting enzyme inhibitor, beta-blocker, anti-angina agents, anti-arrhythmic agents, anti-ischaemic agents, vasodilators, bronchodilators, hypolipidaemic agents and antidiabetics.

Another object of the invention is to provide multiparticulate modified release compositions in which a first portion of Nisoldipine is released in a delayed manner and a second portion of Nisoldipine is released in an extended manner.

Another object of the invention is to provide multiparticulate modified release compositions in which a first portion of Nisoldipine is provided in the form of delayed release pellets and a second portion of Nisoldipine is provided in the form of matrix granules. Particularly, said composition is in the form of a tablet.

Another object of the invention is to provide multiparticulate modified release compositions in which the first portion of the active ingredient is release in a delayed or extended manner and the second portion of the active ingredient is released immediately upon administration.

Another object of the invention is to provide multiparticulate modified release compositions in which both portions of active ingredients are released in an extended manner.

SUMMARY OF INVENTION

The present invention provides multiparticulate modified release pharmaceutical composition comprising: (a) a first portion and (b) a second portion, wherein the active ingredient in the first and second portion is same or belong to a different therapeutic class.

Particularly, said multiparticulate compositions releases one or more active ingredient(s) in a modified manner.

According to one aspect, the present invention provides a multiparticulate modified release pharmaceutical composition comprising:
(a) a first portion comprising an active ingredient, at least one surfactant and at least one release modifying agent;

(b) a second portion comprising an active ingredient and optionally a release modifying agent.

Preferably, the active ingredient in the first portion is a calcium channel blocker. Preferably, the active ingredient in the first portion and the second portion is a calcium channel blocker selected from the group comprising Nisoldipine, Nifedipine, Nitrendipine, Nicardipine, Nimodipine, Felodipine, Amlodipine, Aranidipine, Azelnidipine, Barnidipine, Benidipine, Cilnidipine, Clevidipine, Efonidipine, Lacidipine, Lercanidipine, Manidipine, Nilvadipine, Nitrendipine or Pranidipine.

According to another aspect, the present invention provides multiparticulate modified release pharmaceutical compositions wherein the active ingredient present in the first portion and the second portion are same or belong to a different therapeutic class.

According to another aspect, the present invention provides multiparticulate modified release pharmaceutical compositions wherein the first portion provides the release of the active ingredient in a modified manner and the second portion provides the release of the active ingredient in an extended manner. Particularly, said first and second portion of the composition may be in the form of pellets, tablets, mini-tablets, granules, microparticles or nanoparticles.

According to a preferred aspect, the invention provides multiparticulate modified release pharmaceutical compositions wherein the first portion provides the release of the active ingredient in a delayed manner and the second portion provides the release of the active ingredient in an extended manner.

According to another aspect, the present invention provides multiparticulate modified release pharmaceutical compositions wherein the first portion of the active ingredient is release in a delayed or extended manner and the second portion of the active ingredient is released immediately upon administration.

According to another aspect, the invention provides multiparticulate modified release compositions in which both portions of active ingredients are released in an extended manner.

According to another aspect, the present invention provides multiparticulate modified release pharmaceutical compositions wherein the active ingredient present in the first portion is a calcium channel blocker and the active ingredient present in the second portion is selected from the group comprising angiotensin-converting enzyme inhibitor, beta-blocker, anti-angina agents, anti-arrhythmic agents, anti-ischaemic agents, vasodilators, bronchodilators, hypolipidaemic agents and antidiabetics.

According to a preferred aspect, the invention provides multiparticulate modified release pharmaceutical compositions wherein the first portion of the composition is provided in the form of delayed release pellets and the second portion of the composition is provided in the form of matrix granules.

Preferably, the multiparticulate modified release pharmaceutical composition is in the form of multiparticulate tablet or multiparticulate capsule, more preferably as multiparticulate tablet.

Preferably, the active ingredient present in the first portion and the second portion is Nisoldipine. More preferably, the composition is in the form of a multiparticulate tablet. Said compositions of Nisoldipine exhibits a dissolution profile such that after about 2 hours, from about 5% to about 50% of Nisoldipine is released; after about 4 hours, from about 20% to about 90% of Nisoldipine is released; after about 8 hours, from about 40% to about 100% of Nisoldipine is released; after about 12 hours, more than about 80% of Nisoldipine is released.

According to one aspect, the invention provides multiparticulate modified release pharmaceutical composition comprising:
(a) a first portion comprising Nisoldipine, at least one surfactant and at least one release modifying agent;
(b) a second portion comprising Nisoldipine and optionally a release modifying agent.

According to another aspect, the invention provides multiparticulate modified release pharmaceutical composition comprising:
(a) a first portion comprising: the active ingredient loaded on an inert inner core, a delayed release coat and optionally a separating coat between the inner core and delayed release coat;
(b) a second portion comprising: the active ingredient and one or more release modifying polymer.

According to preferred aspect, the invention provides multiparticulate modified release pharmaceutical composition comprising:
(a) a first portion comprising: the active ingredient adsorbed on an inert inner core, a delayed release coat and optionally a separating coat between the inner core and delayed release coat;
(b) a second portion comprising: the active ingredient and one or more release modifying polymer;
wherein said first portion of the active ingredient is released at pH above 5.5.

According to a preferred aspect, the invention provides multiparticulate modified release pharmaceutical composition comprising:
(a) a first portion comprising Nisoldipine loaded on an inert inner core, a delayed release coat and optionally a separating coat between the inner core and delayed release coat;
(b) a second portion comprising Nisoldipine and optionally a release modifying agent;
wherein said first portion of the active ingredient is released at pH above 5.5.

According to another aspect, the present invention provides process for preparation of said multiparticulate modified release compositions.

According to one aspect, the invention provides a process for preparation of multiparticulate modified release pharmaceutical composition comprising:
(a) preparing a first portion comprising: the active ingredient loaded on an inert inner core, a delayed release coat and optionally a separating coat between the inner core and delayed release coat;
(b) preparing a second portion comprising: the active ingredient and one or more release modifying polymer;
(c) formulating the first portion and the second portion into multiparticulate dosage form.

Additional aspects and/or advantages of the present invention will be evident from the description that follows.

DESCRIPTION OF THE INVENTION

Figure 1:
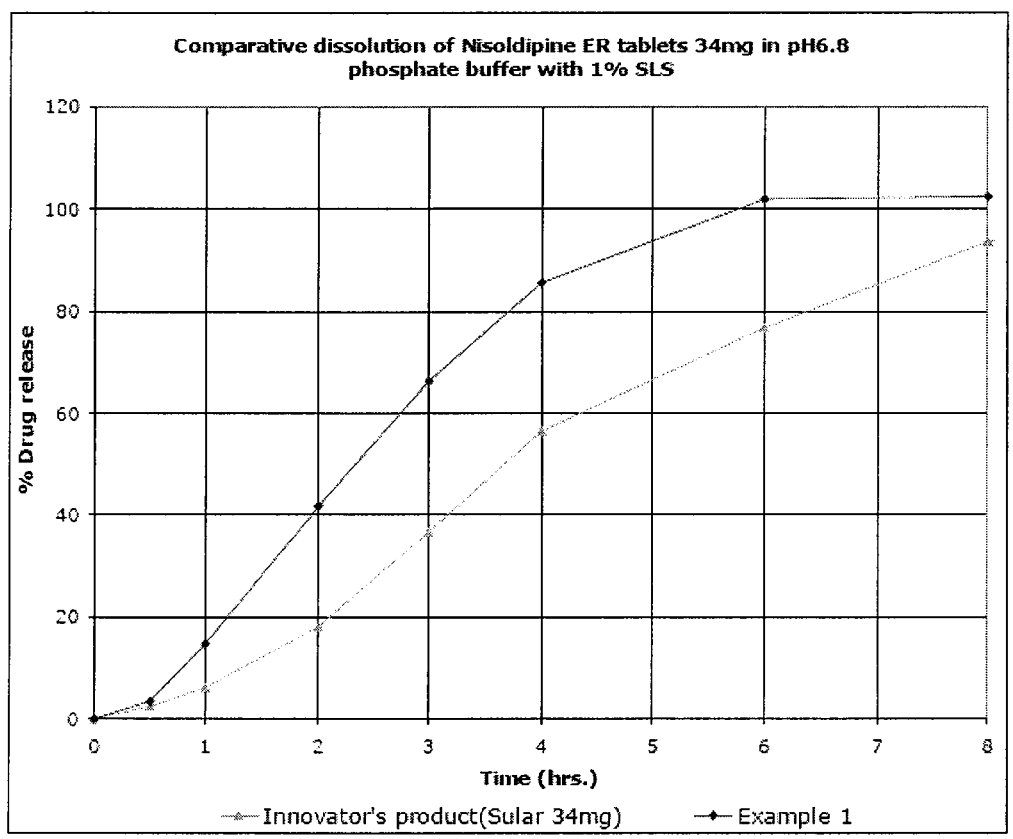
FIG. 1 shows in vitro-dissolution profile of Nisoldipine extended release tablet prepared according to Example 1 of the present invention versus Sular®

The present invention provides multiparticulate modified release pharmaceutical composition comprising: (a) a first portion and (b) a second portion, wherein the active ingredient in the first and second portion is same or belong to a different therapeutic class.

Particularly, said multiparticulate compositions releases one or more active ingredient(s) in a modified manner.

According to one embodiment, the invention provides multiparticulate modified release compositions in which a first portion of the active ingredient is released in a delayed manner upon administration and a second portion of the active ingredient is released in an extended manner, thereby delaying the release of the active ingredient to a region within the gastrointestinal tract and providing greater uptake of the active ingredient as compared to a formulation comprising an enteric polymer coating on the core or a formulation containing polymer which gives the sustained release effect.

The inventors of the present invention have developed compositions which not only give the appropriate drug release from the drug product produced but also improves the bioavailability.

According to one embodiment, the present invention provides multiparticulate modified release pharmaceutical composition comprising:
(a) a first portion comprising an active ingredient, at least one surfactant and at least one release modifying agent;
(b) a second portion comprising an active ingredient and optionally a release modifying agent.

According to one embodiment, the invention provides multiparticulate modified release compositions which provide a combination of two or more different release profiles in a single dosage form.

In the practice of the present invention, the amount of active ingredient present in the first portion and the second portion depend on the dosing regime that is desired.

According to one embodiment, the invention provides multiparticulate modified release compositions wherein the first portion provides the release of the active ingredient in a modified manner and the second portion provides the release of the active ingredient in an extended manner.

According to another embodiment, the invention provides multiparticulate modified release compositions wherein the first portion provides the release of the active ingredient in a delayed manner and the second portion provides the release of the active ingredient in an extended manner.

According to yet another embodiment, the invention provides multiparticulate modified release compositions wherein the first portion of the active ingredient is release in a delayed or extended manner and the second portion of the active ingredient is released immediately upon administration.

According to one embodiment, the present invention provides a multiparticulate modified release composition comprising: (a) a first portion providing the release of the active ingredient in a modified manner and (b) a second portion providing the release of the active ingredient immediately upon administration and/or in a delayed manner and/or in an extended manner; wherein the active ingredient present in the first portion and that of the second portion are either the same or belong to the same or different therapeutic class.

According to one embodiment, the present invention provides multiparticulate modified release compositions providing a first order release followed by zero order release.

According to another embodiment, the present invention provides multiparticulate modified release compositions providing a first order release.

According to one embodiment, the present invention provides multiparticulate modified release compositions wherein the active ingredient in the first portion and the second portion is a calcium channel blocker.

According to a preferred embodiment, the present invention provides multiparticulate modified release compositions wherein the active ingredient in the first portion is a dihydropyridine calcium channel blocker.

The calcium channel blocker may be selected from the group comprising Nisoldipine, Nifedipine, Nitrendipine, Nicardipine, Nimodipine, Felodipine, Amlodipine, Aranidipine, Azelnidipine, Barnidipine, Benidipine, Cilnidipine, Clevidipine, Efonidipine, Lacidipine, Lercanidipine, Manidipine, Nilvadipine, Nitrendipine or Pranidipine.

According to another embodiment, the present invention provides multiparticulate modified release compositions wherein the active ingredient present in the first portion and the second portion are same or belong to a different therapeutic class.

Particularly, said first and second portion of the composition may be in the form of pellets, tablets, mini-tablets, granules, microparticles or nanoparticles.

According to one embodiment, the present invention provides a multiparticulate modified release composition comprising: (a) a first portion providing the release of the active ingredient in a delayed manner and (b) a second portion providing the release of the active ingredient in an extended manner; wherein the active ingredient present in the first portion and that of the second portion are the same.

According to another embodiment, the present invention provides a multiparticulate modified release composition comprising: (a) a first portion providing the release of the active ingredient in a delayed manner and (b) a second portion providing the release of the active ingredient in an extended manner; wherein the active ingredient present in the first portion and that of the second portion belong to the same or different therapeutic class.

According to one embodiment, the present invention provides a multiparticulate modified release composition comprising: (a) a first portion providing the release of the active ingredient in an extended manner and (b) a second portion providing the release of the active ingredient immediately upon administration; wherein the active ingredient present in the first portion and that of the second portion are the same.

In accordance with the features of the present invention, the inventors have developed formulations of Nisoldipine, a dihydropyridine calcium channel blocker. Formulations of other therapeutic drugs may similarly be prepared using the features of the invention.

A wide variety of active agents can be used in conjunction with the present invention. The active agents which may be used according to the present invention include water soluble and water insoluble drugs. Examples of such active agents include antihypertensives, such as inhibitor of angiotensin-converting enzyme, beta-blockers, calcium channel blockers, anti-angina agents, anti-arrhythmic agents, anti-ischaemic agents, angiotensin receptor blockers, vasodilators, bronchodilators, hypolipidaemic agents, antithrombotics, anti-inflammatory agents, diuretics, anti-allergics, skeletal muscle relaxants, antispasmodics, antidiabetics such as insulin sensitizer, insulin secretagogue and the like.

Calcium channels blockers are a group of drugs that slow the entry of calcium into cells by regulating cellular calcium channels. Calcium channel blockers disrupt the calcium (Ca2+) conduction of calcium channels. Clinically calcium channel blockers are used to decrease the blood pressure. Calcium channel blockers work by blocking voltage-gated calcium channels (VGCCs) in cardiac muscle and blood vessels. This decreases intracellular calcium leading to a reduction in muscle contraction. In the heart, a decrease in calcium available for each beat results in a decrease in cardiac contractility. In blood vessels, a decrease in calcium results in less contraction of the vascular smooth muscle and therefore an increase in arterial diameter (CCB's do not work on venous smooth muscle), a phenomenon called vasodilation. Vasodilation decreases total peripheral resistance, while a decrease in cardiac contractility decreases cardiac output. Since blood pressure is determined by cardiac output and peripheral resistance, blood pressure drops.

There are different types of calcium channel blockers such as Dihydropyridine calcium channel blockers, Phenylalkylamine calcium channel blockers, Benzothiazepine calcium channel blockers. Dihydropyridine calcium channel blockers include Nisoldipine, Nifedipine, Nitrendipine, Nicardipine, Nimodipine, Felodipine, Amlodipine, Aranidipine, Azelnidipine, Barnidipine, Benidipine, Cilnidipine, Clevidipine, Efonidipine, Lacidipine, Lercanidipine, Manidipine, Nilvadipine, Nitrendipine or Pranidipine. Phenylalkylamine calcium channel blockers include drugs such as verapamil and Benzothiazepine calcium channel blockers include drugs such as Diltiazem.

Nisoldipine is one of the representative drug belonging to the dihydropyridine calcium channel blocker. Nisoldipine is used in the treatment of hypertension. Nisoldipine is also used in combination with other antihypertensive agents for the treatment of hypertension.

Nisoldipine is a yellow crystalline substance, practically insoluble in water but soluble in ethanol. Nisoldipine has a molecular weight of 388.4. Nisoldipine is 3,5-pyridinedicarboxylic acid, 1,4-dihydro-2,6-dimethyl-4-(2-nitrophenyl)-, methyl 2-methyl-propyl ester, $C_{20}H_{24}N_2O_6$ and has a structure which is represented as below in Formula I, Formula I

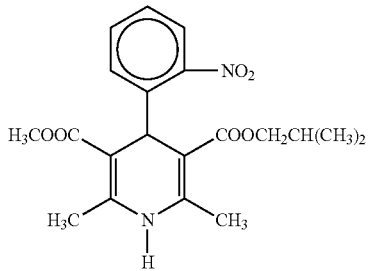

Nisoldipine is marketed as SULAR® by Sciele Pharma, Inc. SULAR® tablets are available as 10 mg, 20 mg, 30 mg or 40 mg of Nisoldipine for once-a-day oral administration. SULAR® tablets were initially developed using core-coat technology. SULAR® tablets consist of an external coat and an internal core. Nisoldipine is present in both core and coat. The core is present as a fast release formulation and coat as slow release formulation. SULAR® tablets developed using Geomatrix® technology are also available as 8.5 mg, 17 mg, 25.5 mg and 34 mg dose of Nisoldipine for once-a-day oral administration.

Prior art discloses various formulations of Nisoldipine. Various attempts have been made to improve the characteristics of controlled release formulations of Nisoldipine. Prior art discloses formulations of Nisoldipine involving the core-coat technology. The disadvantages associated with the core coat technology is that it is a multiple step process and tedious technique. The manufacturing involves use of specialized equipments and the cost of manufacturing is high.

In view of the aforementioned drawbacks associated with prior art compositions it is apparent that there still exists a need for developing a drug delivery system which would ameliorate the aforementioned drawbacks.

According to another embodiment, the present invention provides multiparticulate modified release compositions wherein the active ingredient present in the first portion is a calcium channel blocker and the active ingredient present in the second portion is selected from the group comprising angiotensin-converting enzyme inhibitor, beta-blocker, anti-angina agents, anti-arrhythmic agents, anti-ischaemic agents, vasodilators, bronchodilators, hypolipidaemic agents and antidiabetics.

According to one preferred embodiment, the present invention provides a multiparticulate modified release composition comprising: (a) a first portion providing the release of the active ingredient in a modified manner and (b) a second portion providing the release of the active ingredient immediately upon administration and/or in a delayed manner and/or in an extended manner; wherein the active ingredient present in the first portion and that of the second portion is a calcium channel blocker.

According to a more preferred embodiment, the multiparticulate modified release composition comprises: (a) a first portion providing the release of the active ingredient in a modified manner and (b) a second portion providing the release of the active ingredient immediately upon administration and/or in a delayed manner and/or in an extended manner; wherein the active ingredient present in the first portion and that of the second portion is a Dihydropyridine calcium channel blocker.

According to one embodiment, the present invention provides a multiparticulate modified release composition comprising: (a) a first portion providing the release of the active ingredient in a delayed manner and (b) a second portion providing the release of the active ingredient in an extended manner; wherein the active ingredient present in the first portion and the second portion is a calcium channel blocker selected from the group comprising Nisoldipine, Nifedipine, Nitrendipine, Nicardipine, Nimodipine, Felodipine, Amlodipine, Aranidipine, Azelnidipine, Barnidipine, Benidipine, Cilnidipine, Clevidipine, Efonidipine, Lacidipine, Lercanidipine, Manidipine, Nilvadipine, Nitrendipine or Pranidipine.

According to one preferred embodiment, the present invention provides a multiparticulate modified release composition comprising: (a) a first portion providing the release of the active ingredient in a delayed manner and (b) a second portion providing the release of the active ingredient in an extended manner; wherein the active ingredient present in the first portion and that of the second portion is Nisoldipine.

According to one embodiment, the present invention provides a multiparticulate modified release composition comprising: (a) a first portion providing the release of the active ingredient in an extended manner and (b) a second portion providing the release of the active ingredient immediately upon administration; wherein the active ingredient present in the first portion and the second portion is a Dihydropyridine calcium channel blocker selected from the group comprising Nisoldipine, Nifedipine, Nitrendipine, Nicardipine, Nimodipine, Felodipine, Amlodipine, Aranidipine, Azelnidipine, Barnidipine, Benidipine, Cilnidipine, Clevidipine, Efonidipine, Lacidipine, Lercanidipine, Manidipine, Nilvadipine, Nitrendipine or Pranidipine.

According to one preferred embodiment, the invention provides a multiparticulate modified release composition comprising: (a) a first portion providing the release of the active ingredient in an extended manner and (b) a second portion providing the release of the active ingredient immediately upon administration; wherein the active ingredient present in the first portion and that of the second portion is Nisoldipine. According to another preferred embodiment, the present invention provides a multiparticulate modified release composition comprising: (a) a first portion providing the release of the active ingredient in a delayed manner and (b) a second portion providing the release of the active ingredient immediately upon administration; wherein the active ingredient present in the first portion and that of the second portion is Nisoldipine.

According to one embodiment, the present invention provides a multiparticulate modified release composition comprising: (a) a first portion providing the release of the active ingredient in a delayed manner and (b) a second portion providing the release of the active ingredient in an extended manner; wherein the active ingredient present in the first portion is a calcium channel blocker and the active ingredient present in the second portion is an inhibitor of angiotensin-converting enzyme, beta-blocker, anti-angina agents, anti-arrhythmic agents, anti-ischaemic agents, vasodilators, bronchodilators, hypolipidaemic agents, antidiabetics such as insulin sensitizer, biguanide, insulin secretagogue.

According to one embodiment, the present invention provides a multiparticulate modified release composition comprising: (a) a first portion providing the release of the active ingredient in an extended manner and (b) a second portion providing the release of the active ingredient immediately upon administration; wherein the active ingredient present in the first portion is a calcium channel blocker selected from the group comprising Nisoldipine, Nifedipine, Nitrendipine, Nicardipine, Nimodipine, Felodipine, Amlodipine, Aranidipine, Azelnidipine, Barnidipine, Benidipine, Cilnidipine, Clevidipine, Efonidipine, Lacidipine, Lercanidipine, Manidipine, Nilvadipine, Nitrendipine or Pranidipine and the active ingredient present in the second portion is an inhibitor of angiotensin-converting enzyme.

According to a preferred embodiment, the invention provides a multiparticulate modified release composition comprising: (a) a first portion comprising a calcium channel blocker selected from the group comprising Nisoldipine, Nifedipine, Nitrendipine, Nicardipine, Nimodipine, Felodipine, Amlodipine, Aranidipine, Azelnidipine, Barnidipine, Benidipine, Cilnidipine, Clevidipine, Efonidipine, Lacidipine, Lercanidipine, Manidipine, Nilvadipine, Nitrendipine or Pranidipine and (b) a second portion comprising a beta blocker selected from Acebutolol, Atenolol, Betaxolol, Bisoprolol, Carteolol, Esmolol, Labetalol, Metoprolol, Timolol, Nadolol, Oxprenolol, Penbutolol, Pindolol, Propranolol and Sotalol.

According to a preferred embodiment, the invention provides a multiparticulate modified release composition comprising: (a) a first portion comprising Nisoldipine and (b) a second portion comprising Atenolol.

According to another preferred embodiment, the invention provides a multiparticulate modified release composition comprising: (a) a first portion comprising Nisoldipine and (b) a second portion comprising Propranolol.

According to another preferred embodiment, the invention provides a multiparticulate modified release composition comprising: (a) a first portion comprising Nisoldipine or Nifedipine and (b) a second portion comprising an Angiotensin receptor blocker selected from Valsartan, Telmisartan, Irbesartan, Losartan, Candesartan and Olmesartan.

Suitable Angiotensin-Converting Enzyme inhibitors for use in accordance with the present invention include benazepril, captopril, cilazapril, enalapril, fosinopril, lisinopril, moexipril, perindopril, quinapril, ramipril, and trandolapril or pharmaceutically acceptable salts.

Suitable beta-blockers include compounds selected from Acebutolol, Atenolol, Betaxolol, Bisoprolol, Carteolol, Esmolol, Labetalol, Metoprolol, Timolol, Nadolol, Oxprenolol, Penbutolol, Pindolol, Propranolol and Sotalol.

Suitable Angiotensin receptor blockers include Valsartan, Telmisartan, Irbesartan, Losartan, Candesartan and Olmesartan.

Suitable insulin sensitizer consists of a thiazolidinedione which includes compounds selected from the group consisting of Troglitazone, Ciglitazone, Pioglitazone or Rosiglitazone.

Suitable insulin secretagogue include sulphonylureas selected from the group consisting of Glipizide, Glimepiride, Glibenclamide, Gliclazide and the like.

In one embodiment, the multiparticulate modified release composition comprises: (a) a first portion provided in the form of delayed release tablet and (b) a second portion provided in the form of matrix granules; wherein the active ingredient present in the first portion and that of the second portion is Nisoldipine.

In certain embodiment, the first or second portion of the multiparticulate modified release composition providing the release of the active ingredient in a delayed manner may be in the form of delayed release tablets or delayed release pellets or delayed release granules.

In certain embodiment, the first or second portion of the multiparticulate modified release composition providing the release of the active ingredient in an extended manner may be in the form of an extended release tablet or extended release granules or extended release pellets.

In certain embodiment, the portion of the multiparticulate modified release composition that provides the release of the active ingredient immediately upon administration may be in the form of tablets, capsules, pellets, granules or powders.

According to one embodiment, the invention provides multiparticulate modified release composition of Nisoldipine comprising: (a) a first portion providing the release of Nisoldipine in a delayed manner and (b) a second portion providing the release of Nisoldipine in an extended manner.

According to one embodiment, the invention provides multiparticulate modified release composition comprising:
  (a) a first portion comprising the active ingredient, at least one surfactant and at least one release modifying agent;
  (b) a second portion comprising the active ingredient and optionally a release modifying agent.

According to one embodiment, the invention provides multiparticulate modified release composition comprising:
  (a) a first portion comprising the active ingredient, at least one surfactant and at least one release modifying agent;
  (b) a second portion comprising the active ingredient and optionally a release modifying agent;
wherein said first portion of the active ingredient is released at pH above 5.5

According to one embodiment, the invention provides multiparticulate modified release composition comprising:

(c) a first portion comprising Nisoldipine, at least one surfactant and at least one release modifying agent;

(d) a second portion comprising Nisoldipine and optionally a release modifying agent.

According to one embodiment, the invention provides multiparticulate modified release composition comprising:
(a) a first portion comprising: the active ingredient loaded on an inert inner core, a delayed release coat and optionally a separating coat between the inner core and delayed release coat.
(b) a second portion comprising: the active ingredient and one or more release modifying polymer.

According to one embodiment, the invention provides multiparticulate modified release composition comprising:
(a) a first portion comprising: the active ingredient loaded on an inert inner core, a delayed release coat and optionally a separating coat between the inner core and delayed release coat;
(b) a second portion comprising: the active ingredient and one or more release modifying polymer;
wherein said first portion of the active ingredient is released at pH above 5.5

According to one embodiment, the invention provides multiparticulate modified release composition comprising:
(a) a first portion comprising Nisoldipine adsorbed on an inert inner core, a delayed release coat and optionally a separating coat between the inner core and delayed release coat.
(b) a second portion comprising Nisoldipine and one or more release modifying polymer.

According to one embodiment, the first portion of Nisoldipine is provided in the form of delayed release pellets and the second portion of the composition is provided in the form of matrix granules.

The inert inner core according to the invention is either non-pareil seeds or sugar spheres. Spheres of sugars like dextrose, lactose, anhydrous lactose, spray-dried lactose, lactose monohydrate, mannitol, starches, sorbitol, or sucrose may be used. The drug is loaded onto the inert inner core and the core may optionally be seal coated and further coated with delayed release polymer.

Preferably, the multiparticulate modified release composition of Nisoldipine is in the form of a multiparticulate tablet. Said Nisoldipine compositions may be provided in a dose of 8.5 mg, 17 mg, 25.5 mg and 34 mg.

According to one embodiment, said multiparticulate tablet composition of Nisoldipine exhibits a dissolution profile such that after about 2 hours, from about 5% to about 50% of Nisoldipine is released; after about 4 hours, from about 20% to about 90% of Nisoldipine is released; after about 8 hours, from about 40% to about 100% of Nisoldipine is released; after about 12 hours, more than about 80% of Nisoldipine is released.

According to another embodiment, the multiparticulate modified release composition of Nisoldipine comprises:
(1) a first delayed release portion comprising: active ingredient loaded on an inert inner core; optionally a separating coat on the inner core and a delayed release coat thereon;
(2) a second extended release portion comprising: drug in combination with at least one extended release polymer and suitable pharmaceutical excipients;
wherein said modified release composition exhibits a dissolution profile such that after about 2 hours, from about 5% to about 50% of Nisoldipine is released; after about 4 hours, from about 20% to about 90% of Nisoldipine is released; after about 8 hours, from about 40% to about 100% of Nisoldipine is released; after about 12 hours, more that about 80% of Nisoldipine is released.

According to preferred embodiment, the modified release composition comprises about 2.0% to about 20% by weight of Nisoldipine, about 10% to about 50% by weight of release modifying agents, 2% to about 90% by weight of diluents, about 2% to about 20% by weight of binders, about 0.2% to about 3.0% by weight of lubricants, about 0.2% to about 5% by weight of glidants, about 2.0 to about 20% by weight of coating agents.

According to one embodiment, the delayed release pellets comprises: (a) an inert core; (b) a drug layer applied to the inert core comprising: Nisoldipine and a surfactant (c) optionally, a separating coat on the drug loaded core and (d) a delayed release coating surrounding the drug layer.

According to one embodiment, the delayed release pellets comprises: (a) an inert core; (b) a drug layer applied to the inert core comprising: Nisoldipine and a surfactant (c) optionally, a separating coat on the drug loaded core and (d) a delayed release coating surrounding the drug layer; wherein the delayed release coating comprises a delayed release polymer such as methacrylate derivative or their mixtures.

According to one embodiment, the delayed release pellets comprises: (a) an inert core; (b) a drug layer applied to the inert core comprising: Nisoldipine and a surfactant (c) optionally, a separating coat on the drug loaded core and (d) a delayed release coating surrounding the drug layer; wherein the delayed release coating comprises a delayed release polymer selected from the group consisting of methacrylic acid copolymers.

According to another embodiment, the present invention provides a process for preparation of modified release compositions; said process facilitating the incorporation of high amount of active ingredient/(s) in a single dosage form.

In one embodiment, the present invention provides a process for preparation of multiparticulate modified release composition of Nisoldipine, said process comprising:
(a) preparing delayed release pellets comprising: drug adsorbed on an inert inner core, a delayed release coat and optionally a separating coat between the inner core and delayed release coat;
(b) preparing extended release granules comprising Nisoldipine and optionally a release modifying agent;
(c) blending the delayed release pellets of step (a) and the extended release granules of step (b) with suitable pharmaceutical excipients and compressing into multiparticulate tablets.

According to one embodiment, the invention provides a process for preparation of multiparticulate modified release pharmaceutical composition comprising:
(a) preparing a first portion comprising: the active ingredient adsorbed on an inert inner core, a delayed release coat and optionally a separating coat between the inner core and delayed release coat;
(b) preparing a second portion comprising: the active ingredient and one or more release modifying polymer;
(c) formulating the first portion and the second portion into multiparticulate dosage form.

According to a preferred embodiment, the invention provides a process for preparation of multiparticulate modified release pharmaceutical composition comprising:
(a) preparing a first portion of delayed release pellets comprising the active ingredient adsorbed on an inert inner core, a delayed release coat and optionally a separating coat between the inner core and delayed release coat;

(b) preparing a second portion of matrix granules comprising the active ingredient and one or more release modifying polymer;
(c) mixing the delayed release pellets and matrix granules and further lubricating the mixture;
(d) compressing the lubricated mixture into multiparticulate tablet.

According to a preferred embodiment, the invention provides a process for preparation of multiparticulate modified release pharmaceutical composition comprising:
(a) preparing a first portion of delayed release pellets comprising the active ingredient adsorbed on an inert inner core, a delayed release coat and optionally a separating coat between the inner core and delayed release coat;
(b) preparing a second portion of matrix granules comprising the active ingredient and one or more release modifying polymer;
(c) mixing the delayed release pellets and matrix granules and further lubricating the mixture;
(d) filling the lubricated mixture into capsule.

According to one embodiment, the invention provides a process for preparation of multiparticulate modified release pharmaceutical composition comprising:
(a) preparing a first portion comprising Nisoldipine adsorbed on an inert inner core, a delayed release coat and optionally a separating coat between the inner core and delayed release coat;
(b) preparing a second portion comprising Nisoldipine and one or more release modifying polymer;
(c) formulating the first portion and the second portion into multiparticulate dosage form.

According to one embodiment, the invention provides a process for preparation of multiparticulate modified release pharmaceutical composition comprising:
(a) preparing a first portion comprising Nisoldipine adsorbed on an inert inner core, a delayed release coat and optionally a separating coat between the inner core and delayed release coat;
(b) preparing a second portion comprising Nisoldipine and one or more release modifying polymer;
(c) formulating the first portion and the second portion into multiparticulate tablet;
wherein said first portion of the active ingredient is released at pH above 5.5 and wherein said wherein the composition exhibits a dissolution profile such that after about 2 hours, from about 5% to about 50% of Nisoldipine is released; after about 4 hours, from about 20% to about 90% of Nisoldipine is released; after about 8 hours, from about 40% to about 100% of Nisoldipine is released; after about 12 hours, more than about 80% of Nisoldipine is released.

According to one embodiment, the invention provides a process for preparation of multiparticulate composition comprising:
(a) preparing delayed release pellets comprising Nisoldipine;
(b) preparing extended release granules comprising Nisoldipine;
(c) blending the delayed release pellets and extended release granules and
(d) compressing the blended mixture into multiparticulate tablet.

According to one embodiment, the process for preparation of delayed release pellets of Nisoldipine comprises:
(a) providing an inert core;
(b) preparing a dispersion comprising a binder, an anti-foaming agent and surfactant;
(c) adding the active ingredient into the dispersion of step (b);
(d) optionally adding an anti-foaming agent;
(e) loading the active ingredient dispersion of step (c) or step (d) on to the inert core to form active ingredient loaded inert core;
(f) optionally seal coating the active ingredient loaded inert core;
(g) coating the active ingredient loaded inert core with enteric coating polymer.

According to a preferred embodiment, the process for preparation of delayed release pellets of Nisoldipine comprises:
(a) providing an non pareil seeds;
(b) preparing a dispersion comprising hydroxypropyl methyl cellulose, sodium lauryl sulfate and talc;
(c) adding Nisoldipine into the dispersion of step (b);
(d) optionally adding simethicone emulsion;
(e) loading Nisoldipine dispersion of step (c) or step (d) on to the non pareil seeds to form Nisoldipine loaded non pareil seeds;
(f) optionally seal coating the Nisoldipine loaded non pareil seeds;
(g) coating the Nisoldipine loaded non pareil seeds with Eudragit FS 30D.

According to one embodiment, the invention provides a process for preparation of Nisoldipine extended release granules comprising granulating Nisoldipine with at least one release modifying agent by dry granulation or wet granulation method to form a granules.

According to a preferred embodiment, the invention provides a process for preparation of Nisoldipine extended release granules comprising:
(a) mixing Nisoldipine with hydroxypropyl cellulose, lactose monohydrate and sodium lauryl sulfate;
(b) granulating the mixture of step (a) using purified water or organic solvents such as isopropyl alcohol, methylene chloride to form granulating mass;
(c) drying the mass and further milling the mass to form granules.

According to one embodiment, the invention provides a process for preparation of Nisoldipine extended release composition comprising granulating Nisoldipine with at least one release modifying agent to form a granulate mass; characterized in that the granulation of the mixture is carried out by hot melt granulation at a temperature of 40° C. to 120° C.

The pharmaceutical composition of the invention can also be manufactured by various methods such as by direct compression, dry granulation, wet granulation, double compression, melt granulation, extrusion spheronization and the like.

The surfactants which may be used include, but are not limited to, fatty acids, polysorbate 80, alkyl sulfates, sodium lauryl sulfate, sodium dodecyl sulfate, citric acid or mixtures thereof and may be present in an amount from about 0.5% to about 25% by weight of the total composition.

Delayed release polymers that may be used in accordance with the invention includes cellulose acetate phthalate, polyvinylacetate phthalate, methylcellulose phthalate, ethylhydroxycellulose phthalate, hydroxypropylmethyl cellulose phthalate, cellulose acetate succinate, acetate trimellitate, polyvinyl butyrate acetate, vinyl acetate-maleic anhydride copolymer, styrene-maleic mono-ester copolymer, cellulose derivatives, such as ethylcellulose, a cellulose ester, shellac, polyvinyl alcohol, sodium alginate, methyl acrylate-methacrylic acid copolymer, methacrylate-methacrylic acid-octyl acrylate copolymer or shellac.

In certain embodiment, a separating coat is present between the inner core and delayed release coat. In the practice of the present invention, the separating coat comprises a hydrophilic polymer such as a cellulose derivative polymer. Examples of hydrophilic polymers include hydroxypropyl methylcelluloses, hydroxypropylcelluloses and other cellulose derivatives.

The delayed release pellets may optionally be mixed with conventional tabletting excipients and compressed into a tablet or loaded into a capsule. In certain embodiments, the delayed release pellets may be mixed with extended release granules/pellets and conventional tabletting excipients and compressed into tablets or loaded into a capsule. In certain embodiments, the core is in the form of pellets, beads, powder particles, granules, mini-tablets, micro-tablets, spheroids or microspheres.

In one embodiment, the drug loaded pellets may optionally be coated with an enteric coating polymer. Particularly, said compositions are in the form of a tablet dosage form comprising of pellets and granules compressed together. The enteric coating polymers may be pH dependent polymer and/or pH independent polymers.

The pH dependent polymer may be selected from the group consisting of a polymethacrylate such as copolymers of methylmethacrylate-methacrylic acid and polyvinyl acetate phthalate, a cellulosic ester such as cellulose acetate phthalate, hydroxymethylcellulose phthalate and hydroxypropyl methylcellulose phthalate. Commercially available pH dependent polymers include Eudragit L100-55, Eudragit S100, Eudragit L 30 D-55 and Eudragit FS 30D.

The pH independent polymer may be selected from the group consisting of a cellulosic ether such as methyl cellulose, ethyl cellulose, carboxy methyl cellulose, hydroxy propyl cellulose, hydroxy ethyl cellulose and hydroxy propyl methyl cellulose.

In one embodiment, the invention provides an extended release portion comprising: (i) Nisoldipine or a pharmaceutically acceptable salt thereof; (ii) at least one of the release modifying agents selected from (a) one or more water soluble materials; (b) one or more water insoluble materials; (c) one or more water swellable materials.

The release-modifying agents may have different water solubility and permeability. In the practice of the present invention, the release-modifying agents may be selected from one or more water-soluble release-modifying agent and/or water-insoluble release-modifying agent and/or water-swellable release-modifying agent.

Water soluble release-modifying agents that may be employed for the manufacture of multiparticulate modified release compositions include, but are not limited to polyethylene oxide (average molecular weight 1,00,000 to 50,00,000), sodium alginate, calcium ammonium alginate, potassium alginate, calcium alginate, cellulose derivative polymer like cellulose esters and cellulose ethers (eg. various grades of hydroxypropyl methyl cellulose), propylene glycol alginate, polyvinyl alcohol, povidone, carbomers, xanthan gum, triethyl citrate, a co-polymer of vinylacetate and vinylpyrrolidone (Kollidon SR from BASF) and the like. Water-soluble materials may be present in an amount from about 10% to about 50% by weight of the total composition.

Water-insoluble release-modifying agents that may be employed for the manufacture of multiparticulate modified release compositions include, but are not limited to stearic acid, glyceryl monostearate, glyceryl behenate, glyceryl palmitostearate, microcrystalline wax, polymethacrylate, stearyl alcohol, cetyl alcohol, cetostearyl alcohol, hydrogenated castor oil, polyvinyl acetate phthalate, waxes, shellac, tristearin, rosin, polyvinyl chloride powder or polyethylene powder, magnesium or aluminium silicates and the like and may be present in an amount from about 10% to about 50% by weight of the total composition.

Water-swellable release-modifying agents that may be employed for the manufacture of multiparticulate modified release compositions include, but are not limited to alginic acid, carragenan, xanthan gum, guar gum and the like and may be present in an amount from about 10% to about 50% by weight of the total composition.

Mixtures of water soluble and/or water-swellable release-modifying agents with water-insoluble release-modifying agents may be employed in a weight ratio of about 1:1 to 1:10.

Suitable pharmaceutically acceptable excipients that can be used according to the present invention include, but are not limited to diluents, binders, glidants, lubricants, solvents, rate controlling polymers, pore formers, plasticizers and like.

The diluents which may be used include, but are not limited to, lactose monohydrate, lactose anhydrous, mannitol, starch, pregelatinised starch, lactitol monohydrate, microcrystalline cellulose, dibasic calcium phosphate or mixtures thereof and is present in an amount from about 10% to about 90% by weight of the total composition.

The binders which may be used include, but are not limited to, ethyl cellulose, hydroxypropyl methyl cellulose, hydroxyethyl cellulose, hydroxyethylmethyl cellulose, hydroxypropyl cellulose, methylcellulose, cellulose acetate, cellulose acetate butyrate, polyvinyl alcohol, polyvinyl acetate, polyacrylate, alginic acid, sodium alginate, gelatin, starch, clays, naturally occurring gums, polyvinyl pyrrolidone, copovidone or mixtures thereof and may be present in an amount from about 2% to about 20% by weight of the total composition.

The lubricants which may be used include, but are not limited to, magnesium stearate, colloidal silicon dioxide, stearic acid, talc, hydrogenated castor oil, hydrogenated vegetable oil, sodium stearyl fumarate or mixtures thereof and may be present in an amount from about 0.5% to about 3% by weight of the total composition.

The plasticizers which may be used include, but are not limited to, dibutyl phthalate, dibutyl sebacate, diethyl phthalate, dimethyl phthalate, glycerin, propylene glycol, triacetin, tributyl citrate and triethyl citrate and may be present in an amount from about 0.5% to about 25% by weight of the total composition.

Solvents that may be employed for the coating include isopropyl alcohol, methylene chloride or mixtures thereof. Barrier coating may be performed using Opadry, a ready mix coating material.

Granulation may be carried out using high shear mixer or by spray granulation technique. Mixing and granulation can be carried out in a conventional rapid mixer granulator and the wet granules can be further dried using fluid bed drier. High shear granulation improves the cohesiveness of particles and provides excellent flowability and compression characteristics to the tablet. As the granules exhibit good flow properties, mini tablets produced possess uniformity in weight.

In the practice of the present invention, aqueous/non-aqueous granulation is carried out by adding the binder slowly in a thin stream continuously using a peristaltic pump under high speed mixing with the impeller 'on' and chopper 'off'. On completion of binder addition, mixing is continued at high impeller speed till cohesive granular mass is obtained. If the mass is lumpy then chopper may be used at high speed with impeller also at high speed to obtain uniform wet mass. Drying of granulated mass may be carried out using fluidized bed drier or tray drier. Granulated mass is dried for sufficient time till loss on drying value in the range of about 0.5% to about 3.0% is achieved. In a conventional fluid bed processor both the steps of granulation and drying can be carried out in the same equipment thereby simplifying the process and saving the processing time.

Compression may be carried out using equipments known in the art such as a rotary tablet press or any suitable tabletting machine fitted with suitable size punches and dies. Coating may be carried out using equipments known in the art such as spray coating or coating in conventional coating pan or perforated pans.

The pharmaceutical compositions of Nisoldipine as described herein withstand the accelerated stability conditions of temperature and relative humidity and maintain their physical and chemical integrity at accelerated conditions of stability.

According to one embodiment, the present invention provides a method of treating a patient suffering from hypertension, comprising administering to a patient in need thereof a therapeutically effective amount of Nisoldipine in multiparticulate modified release composition as described herein.

Advantages of the Present Invention

One advantage of the invention is that it allows the incorporation of high amount of active ingredient in the single dosage unit with the different drug release profile.

Another advantage of the invention is that it provides compositions which have better patient compliance as the frequency of dosing is reduced.

Modified release pharmaceutical composition as described herein provides the following advantages,
(1) flexibility in attaining different release patterns,
(2) low risk of dose dumping,
(3) reduced risk of systemic toxicity and increased drug safety,
(4) patient compliance due to reduced frequency of dosing,
(5) reproducibility.
(6) increased bioavailability The process for preparation of the multiparticulate compositions as described herein is easy, less time consuming and economic in comparison to the prior art processes.

As used herein, the term "excipient" refers to a pharmaceutically acceptable ingredient that is commonly used in the pharmaceutical technology for preparing granules and/or solid oral pharmaceutical dosage forms.

As used herein the term "multiparticulate" refers to plurality of particles, pellets, granules, beads or mixtures thereof.

As used herein, the term "modified release" is intended to encompass delayed release, pulsatile release, extended or sustained release.

As used herein, the term "release modifying agent" is intended to encompass enteric coating agents and rate controlling agents.

As used herein, the term "separating coat" is intended to encompass seal coat, barrier coat or intermediate coat.

As used herein, the term "loaded" is intended to encompass sorption, adsorption or absorption.

As used herein, the term "active ingredient" could be used interchangeably with the term "drug".

As used herein, the term "tablet" is intended to encompass compressed pharmaceutical dosage formulations of all shapes and sizes, whether coated or uncoated.

The present invention is further illustrated by reference to the following examples which does not limit the scope of the invention in any way. It will be apparent to those skilled in the art that many modifications, both to the materials and methods, can be practiced without departing from the purpose and scope of the disclosure.

EXAMPLES

Example 1

Preparation of Delayed Release Pellets

Hydroxypropyl methyl cellulose (Methocel E 5) (47.25 g) was added to water. Sodium lauryl sulphate (112.5 g) was added to it and mixed to dissolve completely. Nisoldipine (193.26 g) and talc (23 g) was added to this mixture and mixed to get a suspension. The suspension was homogenized and simethicone 30% emulsion (9 g) was added to this suspension. The suspension was strained using 60# sieve.

40-60# sugar spheres (448 g) were coated with the drug suspension in glatt fluid bed coater equipped with 9" bottom spray wurster insert. The drug loaded pellets were dried and seal coated with opadry yellow. An aqueous dispersion of Eudragit FS 30D (266.60 g) and triethyl citrate (17 g) was prepared and sprayed onto the drug loaded pellets (equivalent to 10,000 tablets) till a weight gain of approx. 20% was achieved. The delayed release pellets along with the talc was cured at inlet temperature of 50° C. for 1 hr.

Preparation of Granules

The active ingredient Nisoldipine (77.30 g) was mixed with Hydroxypropyl cellulose (Klucel GXF) (360 g), sodium lauryl sulphate (60 g) and lactose monohydrate (134.20 g) and granulated using Isopropyl alcohol. The granulated mass was dried, sized and milled to get granules of required size.

Preparation of Multiparticulate Tablets

Pellets (76.5 g) along with the granules (285.75 g) containing active & polymer, Sodium lauryl sulphate (7.5 g), lactose anhydrous (30 g) were mixed and lubricated with colloidal silicon dioxide (3 g) and magnesium stearate (3.75 g). The blend was compressed into tablets and further film coated with opadry yellow.

In-Vitro Dissolution Study

Table 1 summarizes the in vitro-dissolution profile of the Nisoldipine extended release tablet prepared according to Example 1 of the present invention versus Sular® (Nisoldipine extended release tablet by Innovator prepared by Geomatrix® technology) (ref. FIG. 1). Dissolution was carried out by USP Type I (basket) method using pH6.8 phosphate buffer with 1% SLS.

TABLE 1

| | Drug release (%) | |
|---|---|---|
| Time (Hours) | (Sular ®) | Example 1 |
| 0 | 0 | 0 |
| 0.5 | 2.3 | 3.6 |
| 1 | 6.1 | 14.8 |
| 2 | 18.3 | 41.7 |
| 3 | 36.7 | 66.2 |
| 4 | 56.4 | 85.5 |
| 6 | 76.7 | 101.7 |
| 8 | 93.5 | 102.4 |
| 10 | 98 | |
| 12 | 98.8 | |

Example 2

Preparation of Delayed Release Pellets:

Hydroxypropyl methyl cellulose (Methocel E5) (25 g) was added to water, followed by slow addition of Sodium lauryl sulphate (90 g) and dissolved completely. Nisoldipine (100 g) and talc (19 g) was added to it and mixed to form a suspension.

The suspension was homogenized and simethicone 30% emulsion (6 g) was added to it and strained using 60# sieve. Sugar spheres (40-60#) (239 g) were coated with the drug suspension in glatt fluid bed coater equipped with 9" bottom spray wurster insert. The drug loaded pellets were dried and seal coated with opadry yellow. The seal coated pellets were sprayed with an aqueous dispersion of the extended release polymer membrane Eudragit FS 30D (297.5 g), Talc (48.875 g) and triethyl citrate (10.625 g) till a weight gain of approx. 20% is achieved. The delayed release pellets and talc were cured at inlet temperature of 50° C. for 1 hr.

Preparation of Granules

Nisoldipine (72.8 g) was mixed with Hydroxypropyl cellulose (Klucel GXF) (120 g), sodium lauryl sulphate (57 g) and lactose monohydrate (261.70 g) and granulated using Isopropyl alcohol. The granulated mass was dried, sized and milled to get granules of required size.

Preparation of Multiparticulate Tablets

Delayed release pellets (105 g) and Nisoldipine granules (255.75 g) containing active & polymer, sodium lauryl sulphate (7.50 g), lactose anhydrous (30 g) were mixed and lubricated with colloidal silicon dioxide (3 g) and magnesium stearate (3.75 g). The blend was compressed into tablets and further film coated with opadry yellow.

In-Vitro Dissolution Study

Figure 2:
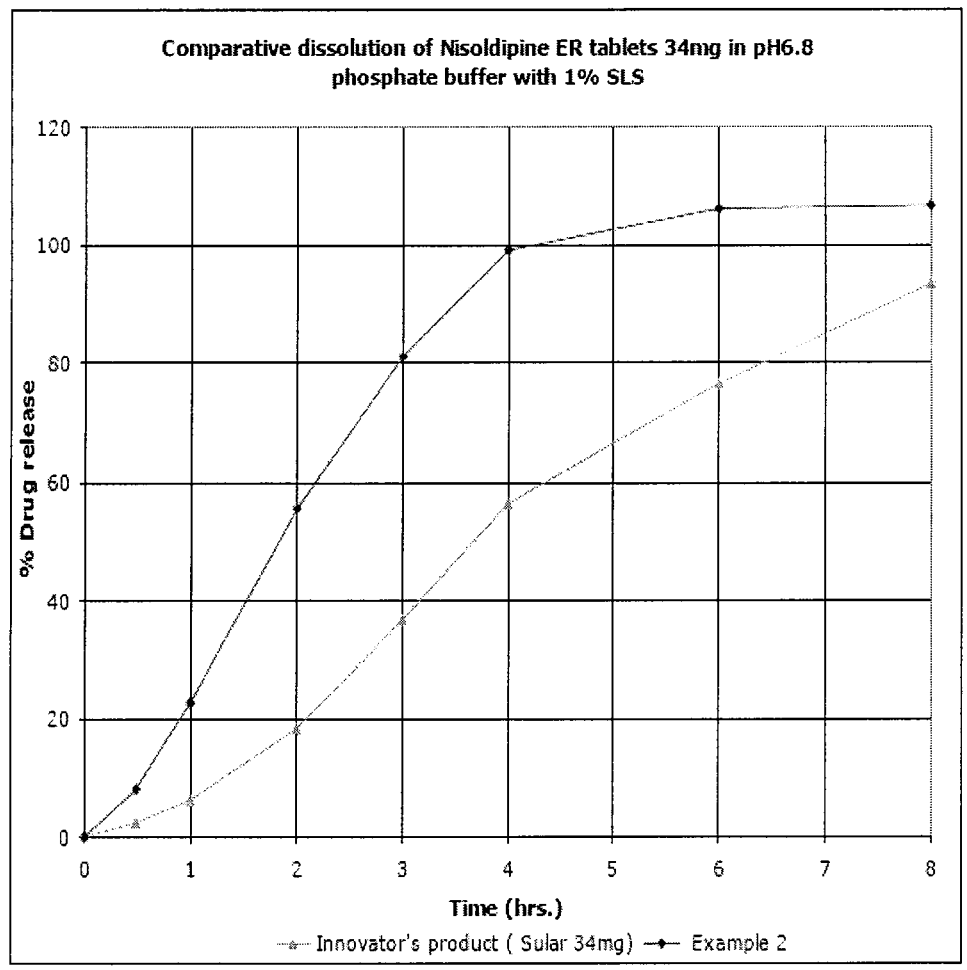
FIG. 2 shows in vitro-dissolution profile of Nisoldipine extended release tablet prepared according to Example 2 of the present invention versus Sular®

Table 2 summarizes the in vitro-dissolution profile of the Nisoldipine extended release tablet prepared according to Example 2 of the present invention versus Sular® (Nisoldipine extended release tablet by Innovator prepared by Geomatrix® technology) (ref. FIG. 2). Dissolution was carried out by USP Type I (basket) method using pH6.8 phosphate buffer with 1% SLS.

TABLE 2

| | Drug release (%) | |
|---|---|---|
| Time (Hours) | (Sular ®) | Example 2 |
| 0 | 0 | 0 |
| 0.5 | 2.3 | 8 |
| 1 | 6.1 | 22.6 |
| 2 | 18.3 | 55.6 |
| 3 | 36.7 | 81.2 |
| 4 | 56.4 | 99.2 |
| 6 | 76.7 | 106.3 |
| 8 | 93.5 | 106.7 |
| 10 | 98 | |
| 12 | 98.8 | |

Bioequivalence Study

A randomized, open label, two treatment, two-period, two sequence, single dose, crossover bioequivalence study was conducted on Nisoldipine extended release tablets prepared according to Example 2 with Sular (Nisoldipine extended release tablets 34 mg) manufactured by Sciele Pharmaceutical as reference product. The study was conducted on 9 normal, healthy, adult, male human subjects under fasting conditions.

The parameters $C_{max}$, $AUC_{0-t}$, $AUC_{0-inf}$ were estimated during the study.

$AUC_{0-t}$=Area under the plasma concentration versus time curve, from time zero to the last measurable concentration.

$AUC_{0-inf}$=Area under the plasma concentration versus time curve, from time zero to infinity.

$C_{max}$=maximum plasma concentration.

The ratios of log transformed mean values for $C_{max}$ and AUC for test and reference (T/R ratio) is a measure of the bioequivalence between the test and reference product.

The summary statistics of pharmacokinetic parameters of Nisoldipine extended release tablets prepared according to Example 2 as test and Sular (Nisoldipine extended release tablets 34 mg) manufactured by Sciele Pharmaceutical as reference are as shown below in Table 3.

TABLE 3

| Parameter | Example 2 Geometric Mean (T) | Reference Geometric Mean (R) | T/R ratio (%) |
|---|---|---|---|
| Cmax (ng/ml) | 4.45 | 3.88 | 114.70 |
| $AUC_{0-t}$ * (ng * hr/ml) | 68.92 | 69.13 | 99.70 |
| $AUC_{0-INF}$ * (ng * hr/ml) | 76.99 | 71.77 | 107.27 |

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

All publications, patents and patent applications are incorporated herein by reference.

We claim:

1. A multiparticulate modified release pharmaceutical composition comprising:
   a first portion comprising
      at least one active ingredient comprising a calcium channel blocker,
      at least one surfactant, and
      at least one release modifying agent; and
   a second portion mixed with the first portion, the second portion comprising
      at least one active ingredient comprising a calcium channel blocker, and
      optionally, at least one release modifying agent,
      the second portion having a different release profile than the first portion;
   the first portion having a form comprising a plurality of at least one selected from pellets, granules, microparticles, nanoparticles, and a combination thereof, the second portion having a form comprising a plurality of matrix granules,
   wherein the active ingredient of the first portion is released at pH above about 5.5, and release of the active ingredient of the second portion is pH independent.

2. The composition as claimed in claim 1, wherein the calcium channel blocker is selected from the group consisting of Nisoldipine, Nifedipine, Nitrendipine, Nicardipine, Nimodipine, Felodipine, Amlodipine, Aranidipine, Azelnidipine, Barnidipine, Benidipine, Cilnidipine, Clevidipine, Efonidipine, Lacidipine, Lercanidipine, Manidipine, Nilvadipine, Nitrendipine, Pranidipine, and combinations thereof.

3. The composition as claimed in claim 1, wherein the active ingredient present in the first portion and the second portion are the same.

4. The composition as claimed in claim 1, wherein the first portion provides the release of the active ingredient in a modified manner and the second portion provides the release of the active ingredient in an extended manner.

5. The composition as claimed in claim 1, wherein the first portion provides the release of the active ingredient in a delayed manner and the second portion provides the release of the active ingredient in an extended manner.

6. The composition as claimed in claim 1, wherein the first portion of the active ingredient is released in a delayed or extended manner and the second portion of the active ingredient is released immediately.

7. The composition as claimed in claim 1, further comprising an active ingredient present in the second portion selected from the group consisting of an angiotensin-converting enzyme inhibitor, beta-blocker, angiotensin receptor blocker, anti-angina agent, anti-arrhythmic agent, anti-ischaemic agent, vasodilator, bronchodilator, hypolipidaemic agent, antidiabetic, and combinations thereof.

8. The composition as claimed in claim 1, further comprising an active ingredient in at least one of the first portion or second portion selected from the group consisting of an angiotensin-converting enzyme inhibitor, beta-blocker, angiotensin receptor blocker, anti-angina agent, anti-arrhythmic agent, anti-ischaemic agent, vasodilator, bronchodilator, hypolipidaemic agent, antidiabetic, and combinations thereof.

9. The composition as claimed in claim 1, wherein the first portion of the composition is provided in the form of delayed release pellets and the second portion of the composition is provided in the form of matrix granules.

10. The composition as claimed in claim 1, wherein the active ingredient present in the first portion and the second portion is Nisoldipine.

11. The composition as claimed in claim 10, wherein the composition is in the form of multiparticulate tablet or capsule.

12. The composition as claimed in claim 10, wherein the first portion of the composition is provided in the form of delayed release pellets and the second portion of the composition is provided in the form of matrix granules and said composition exhibits a dissolution profile such that
after about 2 hours, about 5% to about 50% of Nisoldipine is released,
after about 4 hours, about 20% to about 90% of Nisoldipine is released,
after about 8 hours, about 40% to about 100% of Nisoldipine is released, and
after about 12 hours, more than about 80% of Nisoldipine is released.

13. The composition as claimed in claim 10, wherein the composition comprises about 2.0% to about 20% by weight of Nisoldipine, about 10% to about 50% by weight of release modifying agents, 2% to about 90% by weight of diluents, about 2% to about 20% by weight of binders, about 0.2% to about 3.0% by weight of lubricants, about 0.2% to about 5% by weight of glidants, about 2.0 to about 20% by weight of coating agents.

14. The composition as claimed in claim 7, wherein the beta-blocker is selected from the group consisting of Acebutolol, Atenolol, Betaxolol, Bisoprolol, Carteolol, Esmolol, Labetalol, Metoprolol, Timolol, Nadolol, Oxprenolol, Penbutolol, Pindolol, Propranolol, Sotalol, and combinations thereof; the angiotensin receptor blocker is selected from the group consisting of Valsartan, Telmisartan, Irbesartan, Losartan, Candesartan, Olmesartan, and combinations thereof; the angiotensin-converting enzyme inhibitor is selected from the group consisting of benazepril, captopril, cilazapril, enalapril, fosinopril, lisinopril, moexipril, perindopril, quinapril, ramipril, trandolapril, pharmaceutically acceptable salts thereof, and combinations thereof; the insulin sensitizer is a thiazolidinedione selected from the group consisting of Troglitazone, Ciglitazone, Pioglitazone, Rosiglitazone, and combinations thereof; the antidiabetic is a biguanide or an insulin sensitizer selected from the group consisting of Troglitazone, Ciglitazone, Pioglitazone, Rosiglitazone, and combinations thereof, or an insulin secretagogue selected from the group consisting of Glipizide, Glimepiride, Glibenclamide, Gliclazide, and combinations thereof.

15. A multiparticulate modified release tablet comprising:
a first portion comprising
at least one active ingredient comprising Nisoldipine,
at least one surfactant, and
at least one release modifying agent; and
a second portion mixed with the first portion, the second portion comprising
at least one active ingredient comprising Nisoldipine, and
optionally, at least one release modifying agent,
the second portion having a different release profile than the first portion;
the first portion having a form comprising a plurality of at least one selected from pellets, granules, microparticles, nanoparticles, and a combination thereof, the second portion having a form comprising a plurality of matrix granules,
wherein the active ingredient of the first portion is released at pH above about 5.5, and release of the active ingredient of the second portion is pH independent.

16. A multiparticulate modified release pharmaceutical composition comprising:
a first portion comprising
at least one active ingredient comprising a calcium channel blocker loaded on an inert inner core,
a delayed release coat, and
optionally, a separating coat between the inner core and delayed release coat; and
a second portion mixed with the first portion, the second portion comprising
at least one active ingredient comprising a calcium channel blocker, and
one or more release modifying polymers,
the second portion having a different release profile than the first portion;
the first portion having a form comprising a plurality of at least one selected from pellets, granules, microparticles, nanoparticles, and a combination thereof, the second portion having a form comprising a plurality of matrix granules,
wherein the active ingredient of the first portion is released at pH above about 5.5, and release of the active ingredient of the second portion is pH independent.

17. A multiparticulate modified release pharmaceutical composition comprising:
a first portion comprising
at least one active ingredient comprising Nisoldipine loaded on an inert inner core,
a delayed release coat, and
optionally, a separating coat between the inner core and delayed release coat; and
a second portion mixed with the first portion, the second portion comprising
at least one active ingredient comprising Nisoldipine, and
optionally, at least one release modifying agent,
the second portion having a different release profile than the first portion;

the first portion having a form comprising a plurality of at least one selected from pellets, granules, microparticles, nanoparticles, and a combination thereof, the second portion having a form comprising a plurality of matrix granules, wherein said composition exhibits a dissolution profile such that after about 2 hours, about 5% to about 50% of Nisoldipine is released, after about 4 hours, about 20% to about 90% of Nisoldipine is released, after about 8 hours, about 40% to about 100% of Nisoldipine is released, and after about 12 hours, more than about 80% of Nisoldipine is released, wherein the active ingredient of the first portion is released at pH above about 5.5, and release of the active ingredient of the second portion is pH independent.

18. The composition as claimed in claim 1, wherein the surfactant is selected from the group consisting of fatty acids, polysorbate 80, alkyl sulfates, sodium lauryl sulfate, sodium dodecyl sulfate, citric acid, and mixtures thereof.

19. The composition as claimed in claim 1, wherein the release modifying agent is selected from (a) one or more water soluble materials, (b) one or more water insoluble materials, (c) one or more water swellable materials, and combinations thereof.

20. A process for preparation of the multiparticulate modified release pharmaceutical composition as claimed in claim 16, comprising:

preparing the first portion comprising the active ingredient loaded on the inert inner core, the delayed release coat and optionally the separating coat between the inner core and delayed release coat;

preparing the second portion comprising the active ingredient and one or more release modifying polymers; and formulating the first portion and the second portion into the multiparticulate dosage form.

21. The process as claimed in claim 20, wherein the inert inner core is non-pareil seeds, sugar spheres, or a combination thereof.

22. The process as claimed in claim 20, wherein the delayed release coat comprises enteric coating polymers.

23. The process as claimed in claim 22, wherein the enteric coating polymer is a pH dependent polymer, pH independent polymer, or combinations thereof.

24. The process as claimed in claim 20, wherein the composition is in the form of a multiparticulate tablet.

25. A multiparticulate modified release pharmaceutical composition comprising:

a first portion comprising
at least one active ingredient comprising a calcium channel blocker,
at least one surfactant, and
at least one release modifying agent; and a second portion mixed with the first portion, the second portion comprising
at least one active ingredient selected from the group consisting of calcium channel blocker, angiotensin-converting enzyme inhibitor, beta-blocker, angiotensin receptor blocker, anti-angina agent, anti-arrhythmic agent, anti-ischaemic agent, vasodilator, bronchodilator, hypolipidaemic agent, antidiabetic, and combinations thereof, and
optionally, at least one release modifying agent,
the second portion having a different release profile than the first portion;

the first and second portion each independently having a form comprising a plurality of at least one selected from pellets, granules, microparticles, nanoparticles and a combination thereof, wherein the active ingredient of the first portion is released at pH above about 5.5, and release of the active ingredient of the second portion is pH independent.

* * * * *